United States Patent [19]

Long et al.

[11] 4,217,773
[45] Aug. 19, 1980

[54] METHOD OF DETERMINING THE RELATIVE SOLID SOLUTION CONTAMINATE CONTENT OF METALLIC WIRES

[75] Inventors: Allen K. Long, Fulton County; John M. Seibert, DeKalb County, both of Ga.

[73] Assignee: Western Electric Company, Inc., New York, N.Y.

[21] Appl. No.: 33,612

[22] Filed: Apr. 26, 1979

[51] Int. Cl.³ .................... G01N 25/00; G01N 33/20
[52] U.S. Cl. ................................ 73/15.6; 148/128
[58] Field of Search ...................... 73/15.6; 148/128

[56] References Cited

U.S. PATENT DOCUMENTS

| | | |
|---|---|---|
| 2,499,566 | 3/1950 | Bouton et al. . |
| 3,039,297 | 6/1962 | Peter et al. . |
| 3,537,493 | 11/1970 | Hagarman et al. . |
| 3,586,546 | 6/1971 | Averbach et al. . |
| 4,055,445 | 10/1977 | Pops . |
| 4,061,508 | 12/1977 | Morcau ........................ 148/128 |

*Primary Examiner*—S. Clement Swisher
*Attorney, Agent, or Firm*—Robert B. Kennedy

[57] ABSTRACT

A method is disclosed for determining relative solid solution contaminate content of a wire wherein a selected quantity of thermal energy is applied to the wire, the degree of annealment achieved determined, and the quantity of energy applied compared with the annealment achieved.

7 Claims, 5 Drawing Figures

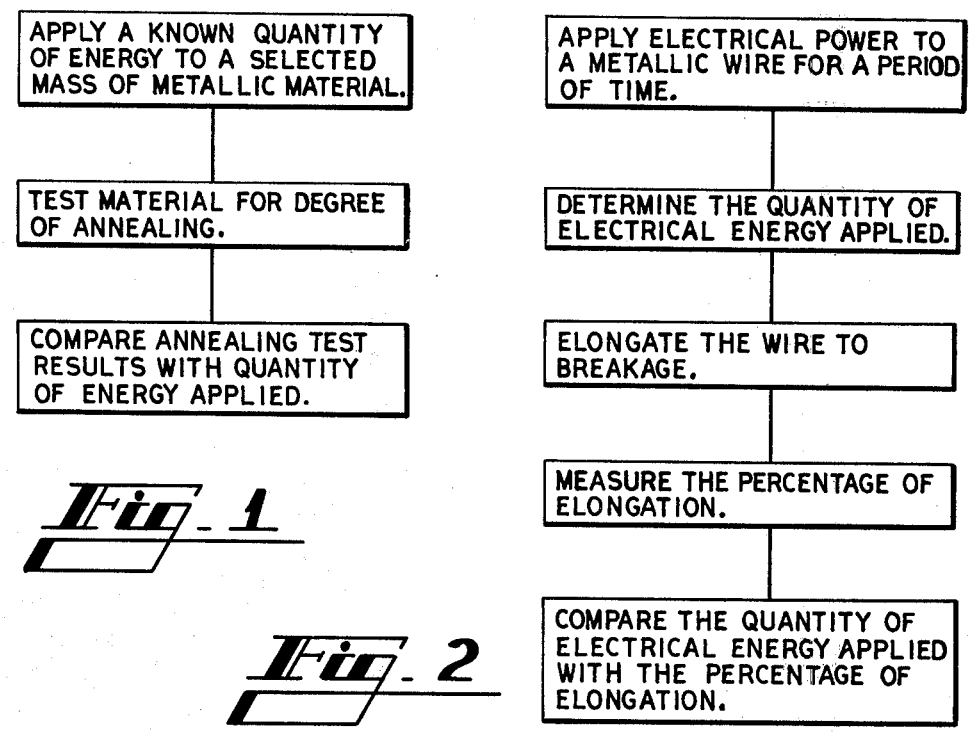
Fig. 1
Fig. 2
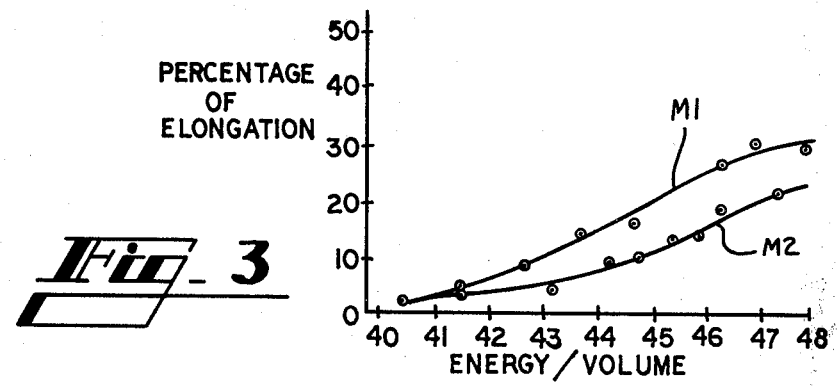
Fig. 3
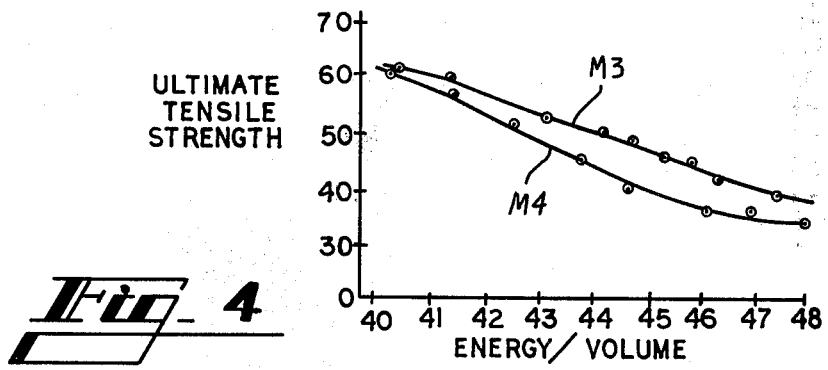
Fig. 4

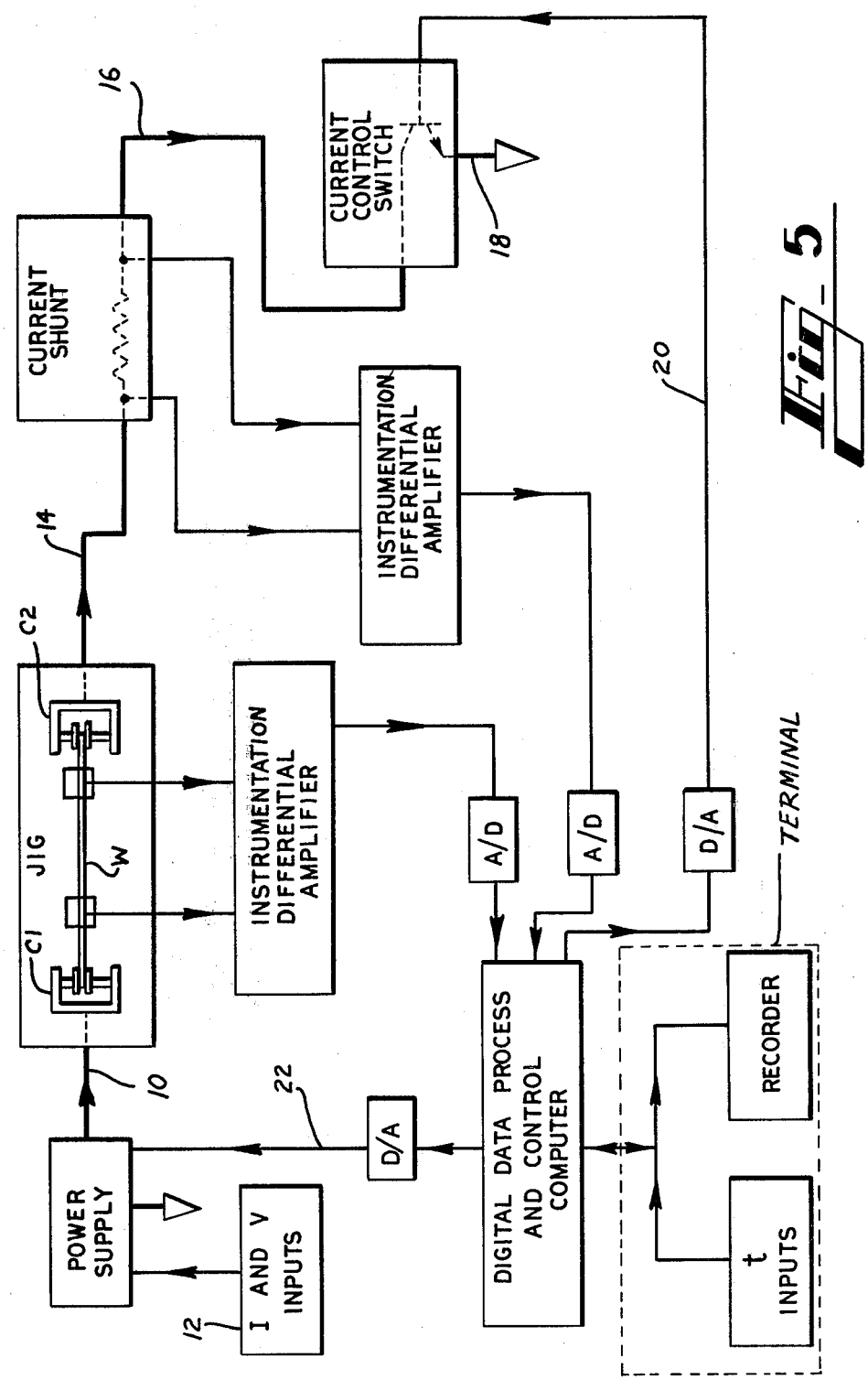

4,217,773

METHOD OF DETERMINING THE RELATIVE SOLID SOLUTION CONTAMINATE CONTENT OF METALLIC WIRES

TECHNICAL FIELD

This invention relates generally to methods of determining the relative purity of metallic wires, and particularly to methods of determining the relative solid solution contaminate content of such wires.

BACKGROUND OF THE INVENTION

In the manufacture of wires for use as conductors in the telecommunications and power distribution industries, it is desirable to know the relative solid solution contaminate content of the conductor material in order to determine to what degree the wire must be annealed to meet flexibility and electrical resistance requirements. If an insufficient amount of power is applied during the annealing process the wire is insufficiently annealed thus reducing its ductility, subjecting it to breakage, and rendering it with excessive electrical resistance. Conversely, if an excessive amount of power is applied during the annealing process a risk of breakage from burn out occurs as well as a waste of energy.

There are, of course, several ways in which the composition of a metallic wire may be anaylzed. For example, the wire may be subject to spectrographic analysis which can render a complete quantitative and qualitative determination of the wire composition. Such a detailed and sophisticated analysis, however, is unneeded and actually inadequate for determining the amount of energy to be applied for annealing. Since such anaylses do not distinguish between the various forms in which impurities are present, such as particulate, inter-metallic compound, or solid solution. These various forms occur in accordance with the thermal history of the wire. A copper wire containing one impurity in particulate form, for example, will anneal better than one containing the same quantity of that impurity in solid solution form, thus causing a substantial degradation in wire annealability.

Another well known approach in determining the degree of purity of conductive wire material involves the use of electrical conductivity testing. Again, however, the conductivity of a metallic wire is a function of both the proportion as well as the composition of the impurities present. The measurement of conductivity alone therefore can lead to an erroneous determination of material purity as far as annealing characteristics are concerned.

It is thus seen that a need exists for a method of determining the solid solution contaminate content of wire conductive material which is accurate, practical for use in a manufacturing environment, and not unduly sophisticated as by producing an analysis of the impurities themselves. It is to this task to which the present invention is primarily directed.

SUMMARY OF THE INVENTION

In a general form of the invention a method is provided for determining the relative solid solution contaminate content of a wire which comprises the steps of applying a selected quantity of thermal energy to the wire, testing the wire for the degree of annealing thereby achieved, and comparing the annealing test results with the quantity of thermal energy applied.

In a more specific form of the invention a method is provided for determining the relative solid solution contaminate content between two wire samples drawn from two different batches of conductive materials, the principal constituents of which are known. Here the method comprises the steps of applying known and mutually different discrete quantities of electric energy to a plurality of longitudinal segments of each wire sample, determining the degree of annealment achieved on each segment of each wire sample, and comparing the annealment achieved versus the quantity of electric energy applied between the segments of the two wires.

BRIEF DESCRIPTION OF THE DRAWINGS

FIG. 1 is a block diagram of a preferred method of the invention in one preferred form.

FIG. 2 is a block diagram of a preferred method of the invention in another preferred form.

FIG. 3 is a graph illustrating the percentage of elongation versus energy per volume applied, which is a function of relative solid solution contaminate content, of two copper wire samples as actually determined in accordance with the invention.

FIG. 4 is another graph illustrating ultimate tensile strength versus energy per volume applied, which also is a function of relative solid solution contaminate content, of two copper wires as also determined in accordance with the invention.

FIG. 5 is a block diagram of apparatus which may be employed in practicing the invention.

DETAILED DESCRIPTION

As portrayed in FIG. 1, in its general form the present method comprises the steps of applying a known quantity of energy to a metallic material, testing the material for the degree of annealing thereby achieved, and comparing the annealing test results with the quantity of energy applied. In the more specific form shown in FIG. 2 electric power is applied to a metallic wire for a period of time and the quantity of energy applied determined. The wire is then elongated to breakage and the percentage of elongation measured. The quantity of electrical energy is then compared with the percentage of elongation measured.

In FIG. 5 apparatus is illustrated with which electric power may be applied to a metallic wire for a period of time and the quantity of electrical energy applied determined. The apparatus is seen to include a jig to which a wire W is mounted extending between two clamps C1 and C2. A direct current supply, which includes control means 12 establishing a general level of voltage and current to be applied to the wire, is connected by power line 10 to jig clamp C1. Other power lines 14, 16 and 18 connect the other jig clamp C2 to ground through a current shunt and a current control switch.

The apparatus is further seen to include a digital data process and control computer to which a terminal is connected comprised of means for inputting selected time periods t and for recording the quantity of energy applied to the wire during such time periods. An instrumentation differential amplifier is coupled across the wire W by a conventional Kelvin connection means in order to measure and amplify the voltage across the wire and to input a signal to the computer in digital form indicative thereof through an analogue to digital converter. Another instrumentation differential amplifier is coupled across the current shunt for measuring the current passing through the shunt, and thus through wire W in series circuit therewith, and for inputting a signal to the computer in digital form indicative thereof through another analogue to digital converter. The apparatus further includes a control line 20 operatively coupling the current control switch with the computer through a digital to analogue converter. Another control line 22 couples the computer with the power supply through another digital to analogue converter for adjusting the power supply voltage as needed to maintain a reasonably constant, selected level of current through the test wire W as it becomes heated. One set of components which may be used for the apparatus just described is as follows:

TABLE I

| | |
|---|---|
| Power Supply | Hewlett Packard Model No. 6469, 0–35 VDC, 0–300 amps |
| Current Shunt | Empro 50 millivolts per 100 amps |
| Current Control Switch | 3 parallel 100 amp transistors type STC 9178 |
| Instrumentation Differential Amplifier | 2 L M 741 type operational amplifiers coupled in a differential amplifier configuration |
| Digital Data Process and Control Computer | Hewlett Packard Type 2100 Minicomputer |
| Terminal | Digital Equipment Corporation Model No. LA 36 EE Terminal |
| Analog to digital Converter | Hewlett Packard 91000A Subsystem Interface Card |
| Digital to Analog Convertor | Hewlett Packard 12555 B Type Subsystem Interface Card |

For operation a wire to be tested, such as one composed principally of copper or aluminum, is mounted in the jig and electrically coupled with the amplifier. A time period t is selected and inputted to the computer from the terminal and generally prescribed current and voltage levels established by the power supply. Upon test start the computer closes the current control switch for the time period selected thereby causing electric current to flow from the power supply through the test wire sample. The voltage across the wire is sensed and amplified by one of the instrumentation differential amplifiers and a digitized signal representative of that voltage inputted into the computer. At the same time the current flow through the wire is recognized and amplified by the other instrumentation differential amplifier coupled across the current shunt and a digitized signal representative of that current also inputted to the computer. The level of current flow is maintained generally constant through the wire as it is heated by control signals to the power supply from the computer over control line 22. Once the selected time period t has elapsed the computer opens the current control switch and calculates the total thermal energy applied to the wire by integrating the product increments of voltage and current over time. This is done by application of the formula $$e_t = \int_{t_i}^{t_f} vi\,dt$$

where
 $e_t$ = thermal energy
 $t_i$ = time when electrical power is applied on
 $t_f$ = time when electrical power is terminated
 v = instantaneous voltage
 i = instantaneous current.

Alternatively energy calculations can be done in electrical instead of thermal terms. The result is transmitted to the thermal recorder for display or storage.

Next the wire is removed from the jig and tested to determine the degree of annealment achieved. This may be done in several ways. For example, the wire may be placed in an Instron tensil testing machine and stretched to breakage and the percentage of elongation measured. Alternatively, the ultimate tensil strength may be measured with the same machine.

The just described procedure of applying a known quantity of energy to material and determining the degree of annealment achieved is preferably performed on several segments of a sample of one batch of conductive material at different energy levels. This provides data to plot profile curves such as those shown in FIGS. 3 and 4. In FIG. 3, for example, a curve M1 is shown constructed from eight tests actually performed on eight wire segments cut from one wire sample with eight different energy per wire volume levels. The individual wire segment plots and resulting curve thus produce a graphic illustration of the relative solid solution contaminate content of that wire sample from which the eight segments were taken and tested. In FIG. 3 another curve M2 is shown made from nine tests performed on nine segments cut from another wire sample. As the wire from which curve M1 was drawn is seen to yield a greater percentage of elongation than the wire from which curve M2 was generated, it is evident that the M1 wire has a lesser degree of solid solution contaminate than that of the M2 wire. By establishing norms or minimum acceptable levels of such contaminate, it becomes possible to determine the relative solid solution contaminate content of a wire by performing one test on one wire sample. Several tests, however, are preferred in order to generate a profile that displays more information with regard to the particular batches of material or wire being examined.

FIG. 4 illustrates a plot of ultimate tensile strength versus energy per volume applied to material tested. The curve M3 results from actual testing of nine segments from one wire sample or batch of material while the curve M4 results from the testing of eight segments of material from another wire sample or batch. Here it is seen that the M3 material has greater ultimate tensile strength for a given level of energy per volume applied than that of the M3 material. The M4 material therefore is seen to have the lower level of solid solution contaminate content The just described methods enable a wire manufacturer to examine the quality of material from which wire is drawn. This is done on a relative scale by comparing the solid solution content of a wire tested with a standard or norm or with that of another wire. Measurement of the solid solution content in absolute terms is thus not required.

It should be understood that the just described embodiments merely illustrate principles of the invention in selected, preferred forms. Many modifications, additions and deletions may, of course, be made thereto without departure from the spirit and scope of the invention as set forth in the following claims.

What is claimed is:

1. The method of determining relative solid solution contaminate content of a wire comprising the steps of:
 (a) applying a selected quantity of thermal energy to the wire:

(b) testing the wire for the degree of annealing achieved by step (a) by elongating the wire to breakage; and (c) comparing the results obtained in step (b) with the quantity of thermal energy applied in step (a).

2. The method of determining a relative solid solution contaminate content of a wire in accordance with claim 1 wherein the percentage of elongation achieved to breakage is measured and compared with the quantity of thermal energy applied.

3. The method of determining relative solid solution contaminate content between two wires drawn from two different batches of conductive materials and which comprises the steps of:

(a) applying known and mutally different discrete quantities of electric energy to a plurality of longitudinal segments of each wire;

(b) determining the degree of annealment achieved in step (a) on each segment of each wire; and (c) comparing the annealment achieved versus the quantity of electric energy applied between the segments of the two wires.

4. The method of determining relative solid solution contaminate content between two wires in accordance with claim 3 wherein step (b) each segment of each wire is elongated to breakage.

5. The method of determining relative solid solution contaminate content between two wires in accordance with claim 4 wherein the percentage of elongation achieved to breakage is measured in step (b) on each wire segment and in step (c) against the discrete quantity of electric energy applied on each wire segment.

6. The method of determining relative solid solution contaminate content between two wires in accordance with claim 4 wherein the ultimate tensile strength achieved is measured in step (b) on each wire segment and plotted in step (c) against the discrete quantities of electric energy applied on each segment of the two wires.

7. The method of determining relative solid solution contaminate content between two wires in accordance with claim 3 wherein the results obtained in step (c) are graphically illustrated by two curves extending approximately through plots of energy per wire volume versus annealment achieved for the segments of each wire.

* * * * *